United States Patent
Marechal et al.

(10) Patent No.: US 10,975,399 B2
(45) Date of Patent: Apr. 13, 2021

(54) USE OF NITRIC OXIDE OR NITRIC OXIDE DONOR FOR INDUCING THE PRODUCTION OF TRIACYLGLYCEROLS IN MICROALGAE

(71) Applicant: Commissariat A L'energie Atomique Et Aux Energies Alternatives, Paris (FR)

(72) Inventors: Eric Marechal, Grenoble (FR); Lina Juana Dolch, Grenoble (FR)

(73) Assignee: Commissariat A L'Energie Atomique Et Aux Energies Alternatives, Paris (FR)

( * ) Notice: Subject to any disclaimer, the term of this patent is extended or adjusted under 35 U.S.C. 154(b) by 795 days.

(21) Appl. No.: 15/417,961

(22) Filed: Jan. 27, 2017

(65) Prior Publication Data
US 2017/0218412 A1 Aug. 3, 2017

(30) Foreign Application Priority Data
Jan. 29, 2016 (EP) .................... 16305089

(51) Int. Cl.
C12P 7/64 (2006.01)
C12N 1/12 (2006.01)
C12N 1/38 (2006.01)

(52) U.S. Cl.
CPC ............. *C12P 7/649* (2013.01); *C12N 1/12* (2013.01); *C12N 1/38* (2013.01); *C12P 7/6454* (2013.01); *C12P 7/6463* (2013.01)

(58) Field of Classification Search
CPC ..... C12N 1/12; C12N 1/38; C12P 7/00; C12P 7/6463; C12P 7/649; C12P 7/6454; C12P 7/6436; C10L 2200/0476
See application file for complete search history.

(56) References Cited

U.S. PATENT DOCUMENTS

2011/0045564 A1* 2/2011 Dhamwichukorn ..... C12N 1/06
435/170

FOREIGN PATENT DOCUMENTS

| CN | 105713950 | * 12/2014 |
| CN | 105483013 | * 12/2015 |
| WO | WO 2013/148348 A1 | 10/2013 |
| WO | WO 2015/111029 A1 | 7/2015 |

OTHER PUBLICATIONS

Quinn, John F., et al. "Delivering Nitric Oxide with Nanoparticles." Journal of Controlled Release, vol. 205, 2015, pp. 190-205., doi: 10.1016/j.jconrel.2015.02.007. (Year: 2015).*
Chen et al. "Nitric oxide Plays a Role as Second Messenger in the Ultraviolet-B Irradiated Green Alga Chlorella pyrenoidosa" Folia Microbiol. 55 (1), 53-60 (2010) (Year: 2010).*
Cyanosite "f/2 Medium" from Mar. 29, 2004 2pgs (Year: 2004).*
Zhangbin et al. "Effects of NO and Different Media on the Growth of Prorocentrum micans" Journal of Ocean University of China Jul. 30, 2006, vol. 5, No. 3, pp. 239-242 (Year: 2006).*
European Search Report for Application No. 16 30 5089 dated Jul. 1, 2016.
Adams, C. et al., *Understanding Precision Nitrogen Stress to Optimize theGrowth and Lipid Content Tradeoff in Oleaginous Green Microalgae*, Bioresource Technology, 131 (2013) 188-194.
Lehner, C. et al., *Nitric Oxide Suppresses Growth and Development in the Unicellular Green Alga Micrasterias Denticulata*, Journal of Plant Physiology, 166 (2009) 117-127.
Singh, A. K. et al., *Antioxidative Role of Nitric Oxide on Copper Toxicity to a Chlorophycean Alga, Chlorella*, Ecotoxicology and Environmental Safety, 59 (2004) 223-227.
Abida et al., (2015).
Ball et al., Plant Science 1990, 66:1-9.
Christi, Biotechnology Advances 25 (2007) 294-306.
Christi, Trends in Biotechnology, 2008, vol. 26, No. 3.
Christi, Journal of Biotechnology 167 (2013) 201-214.
Dismukes et al., Current Opinion in Biotechnology 2008, 19:235-240.
Dorval Courchesne et al., Journal of Biotechnology 141 (2009) 31-41.
Durrett et al., The Plant Journal (2008) 54, 593-607.
Micro- and macro-algae: utility for industrial application, Sep. 2007, Editor: Diana Bowles.
Miller et al., British Journal of Pharmacology (2007) 151, 305-321.
Scott et al., Current Opinion in Biotechnology 2010, 21:277-286.
Siaut et al., BMC Biotechnology 2011, 11:7.
Singh et al., Bioresource Technology 102 (2011) 26-34.
St. Laurent, C. D. et al., *Measurement of Nitric Oxide in Mast Cells With the Fluorescent Indicator DAF-FM Diacetate*, Methods Mol. Biol. 1220:339-45.
Vardi et al., (2008).
Zhang et al., Bioresource Technology 147 (2013) 59-64.

* cited by examiner

*Primary Examiner* — Thane Underdahl
(74) *Attorney, Agent, or Firm* — Alston & Bird LLP

(57) ABSTRACT

The invention relates to a method for triggering triacylglycerols (TAG) accumulation in microalgae comprising the step of contacting a source of exogenous nitroxide (NO) with said microalgae in their growth medium.

11 Claims, 2 Drawing Sheets

USE OF NITRIC OXIDE OR NITRIC OXIDE DONOR FOR INDUCING THE PRODUCTION OF TRIACYLGLYCEROLS IN MICROALGAE

FIELD

The invention relates to a method for accumulating triacylglycerols (TAG) in microalgae by adding a nitric oxide donor to the growth medium. The invention also relates to a method for producing fatty acids, biofuels, pharmaceutical or cosmetic compositions, and also food supplements, comprising a triacylglycerols accumulation step in microalgae according to the invention. Finally, the invention relates to the use of a nitric oxide donor to accumulate triglycerides in microalgae.

BACKGROUND

It is acknowledged that oilseed production from crops cannot be diverted from nutritional purpose (Durrett et al., The Plant Journal (2008) 54, 593-607). Therefore, efforts are directed towards the oil production in other organisms like algae (Chisti, Biotechnology Advances 25 (2007) 294-306; Chisti, Trends in Biotechnology, 2008, Vol 26, No. 3; Dismukes et al., Current Opinion in Biotechnology 2008, 19:235-240; Scott et al., Current Opinion in Biotechnology 2010, 21:277-286; Singh et al., Bioresource Technology 102 (2011) 26-34). Studies undergone on triacylglycerol (TAG, also called oil) production in algae (Table 1 below) have focused on the increase of TAG in cytosolic droplets.

TABLE 1

Oil content of some algae (from Chisti, Biotechnology Advances 25 (2007) 294-306)

| Microalga | Oil content (% dry wt) |
|---|---|
| *Botryococcus braunii* | 25-75 |
| *Chlorella* sp. | 28-32 |
| *Crypthecodinium cohnii* | 20 |
| *Cylindrotheca* sp. | 16-37 |
| *Dunaliella primolecta* | 23 |
| *Isochrysis* sp. | 25-33 |
| *Monallanthus solina* | >20 |
| *Nannochloris* sp. | 20-35 |
| *Nannochloropsis* sp. | 31-68 |
| *Neochloris oleoabundans* | 35-54 |
| *Niirschia* sp. | 45-47 |
| *Phaeodacrylum tricornutum* | 20-30 |
| *Schizochytrium* sp. | 50-77 |
| *Tetraselmis sueica* | 15-23 |

The advantages of microalgae over land plants have been summarized in the EPOBIO report (Micro- and macroalgae: utility for industrial application, September 2007, Editor: Dianna Bowles). Both plants (crops) cultivable on arable lands and microalgae grown in open ponds or in confined reactors are potential sources of TAG and fatty acids for industrial purposes and biofuels (Dismukes et al., Current Opinion in Biotechnology 2008, 19:235-240). However, serious concerns have been raised by the intensive agricultural practices, and the diversion of crops from food to non-food chains. Efforts are thus needed to develop novel generation biofuels based on photosynthetic microorganisms.

The main advantages of microalgae in relation to plants for the production of TAG are the following:
- this bioresource does not compete with the agro-resources used for animal or human nutrition.
- algal growth can be monitored in controlled and confined conditions in an environmental friendly process using recycled inorganic and organic wastes generated by other human activities and the use of microalgae allows trapping and converting industrial byproduct gases (e.g. $CO_2$) into valuable organic molecules (Chisti, Biotechnology Advances 25 (2007) 294-306; Chisti, Trends in Biotechnology, 2008, Vol 26, No. 3; Chisti, Journal of Biotechnology 167 (2013) 201-214).
- the algal biomass productivity is high, microalgae showing a very high potential of productivity with cost savings when compared to land plants (see Table 2). Their yield is variable and determined by the culturing approach employed: it is relatively low in open pond systems while it can be significantly increased in closed photobioreactors where culture parameters can be controlled.
- this bioresource does not depend on a geographical location, or on a season.

TABLE 2

Comparison of biomass productivity of major crops ("C3" or "C4" type photosynthesis) and microalgae (extract from the «EPOBIO project» report, University of York (09/2007), Table 4).

| | Microalgae | "C₄" crops (*sorghum*, maize, sugarcane . . . ) | "C₃" crops (wheat, sunflower . . . ) |
|---|---|---|---|
| Maximal productivity ($T \cdot ha^{-1} \cdot y^{-1}$) | | | |
| Microalgae (photobioreactors) | 130 to 150 | — | — |
| Higher plants (maximum productivity) | — | 72 | 30 |
| Average productivity in production systems ($T \cdot ha^{-1} \cdot y^{-1}$) | | | |
| Microalgae (large scale) | 10 to 50 | — | — |
| Higher plants (field) | — | 10 to 30 | 8 to 18 |
| Biomass production costs ($USD \cdot kg^{-1}$) | 0.4-40 | 0.04 | 0.04 |

The economic viability of this sector of bioindustry is challenged by the current limitation to combine the overall biomass yield, i.e. dry weight of algal organic matter produced per liter and the proportion of valuable molecules, i.e. sufficiently high proportion of TAG per dry weight for industrial extraction and processing (Chisti, Biotechnology Advances 25 (2007) 294-306; Chisti, Trends in Biotechnology, 2008, Vol 26, No. 3; Chisti, Journal of Biotechnology 167 (2013) 201-214).

In particular, the lipid composition of microalgae is compatible with biodiesel production (Dismukes et al., Current Opinion in Biotechnology 2008, 19:235-240; Scott et al., Current Opinion in Biotechnology 2010, 21:277-286). The rationale for producing biodiesel from microalgae is to use sunlight to convert water and carbon dioxide into biomass. This biomass is then specifically redirected towards the synthesis of oil for the generation of biofuels, by applying external stimuli like nutrient stresses, and/or by genetic engineering of metabolism (Dorval Courchesne et al., Journal of Biotechnology 141 (2009) 31-41).

The three most important classes of micro-algae in terms of abundance are the green algae (class Chlorophyceae, group Viridiplantae), the diatoms (class Bacillariophyceae, phylum Heterokont, superphylum Chromalveolata) and the golden algae (class Chrysophyceae, phylum Heterokont, superphylum Chromalveolata) (EPOBIO definition). Diatoms are a major phylum of the phytoplankton biodiversity in oceans, fresh water and various soil habitats. They are responsible for up to 25% of the global primary productivity. Study of this group of eukaryotes has benefited from recent developments on *Phaeodactylum tricornutum*, a model of pennate diatoms. Diatoms, like other microalgae, are considered a plausible alternative source of hydrocarbons to replace fossil fuels or chemicals from petrochemistry, with the advantage of having a neutral $CO_2$ balance, based on the hypotheses that $CO_2$ and water can be efficiently converted into biomass by photosynthesis and that the carbon metabolism could be controlled so that they accumulate energetically-rich TAG. Different phytoplanktonic organisms of the Chromalevolata superphylum have focused the attention for their ability to accumulate TAG, with promising initial yields and appropriate robustness and physical properties to be implemented in an industrial process, including *Phaeodactylum tricornutum*. *Phaeodactylum tricornutum* is currently used for the industrial production of omega-3 polyunsaturated fatty acids but industrial implementation for this application and for other applications such as biofuels is still limited by the growth retardation and low yield in biomass when TAG accumulation is triggered using conventional nutrient starvation approaches, such as nitrogen starvation (Chisti, Journal of Biotechnology 167 (2013) 201-214).

Thus, currently, the reduction of the availability of nitrate ($NO_3^-$) in the growth medium is the most used process to trigger the accumulation TAG in microalgae. However, the reduction of the availability of nitrate in the growth medium also blocks the growth of the cells (Adams C, Godfrey V, Wahlen B, Seefeldt L, Bugbee B. Bioresour Technol. 2013, 131, 188-194). Therefore, while the accumulation of TAG is really enhanced by such a process (TAG per microalgal cell), this accumulation is not sufficiently efficient to counterbalance the loss due to growth reduction and as a result, the gain in productivity (TAG per amount of triacylglycerol per volume of microalga culture and per day) is limited.

These approaches have therefore an important drawback, which is the limitation of growth that the nitrogen starvation induces. *Phaeodactylum tricornutum* exhibits interesting properties for an industrial implementation, like the ability to grow in the absence of silicon or the sedimentation of cells that could be useful for harvesting techniques. Attempts to promote TAG accumulation can rely on various strategies that can be combined, including the stimulation of fatty acid and TAG biosynthesis, the blocking of pathways that divert carbon to alternative metabolic routes and eventually the arrest of TAG catabolism. Small molecules could act on each of these three aspects of TAG metabolism.

As another approach, it is possible to promote the accumulation of oil in microorganisms by inhibiting or blocking metabolic pathways that direct the carbon fluxes to alternative metabolites. For instance, it is well known that blocking the accumulation of carbohydrate in storage sugars such as starch, can promote the accumulation of oils (Siaut et al., BMC Biotechnology 2011, 11:7). However, blocking the storage of carbohydrates has a negative impact on cell growth, especially in the dark when these storage carbohydrates are needed to feed cells (Ball et al. Plant Science 1990, 66:1-9), and hence on productivity.

Other metabolic pathways using carbon might be blocked and allow a redirection of carbon metabolism towards TAG metabolism. Thus, an approach based on inhibition of metabolism of sterols has recently been developed (WO 2015/111029).

However, there remains a need for alternative methods able to produce lipid at the highest biomass productivity with the highest lipid cell content.

SUMMARY

Unexpectedly, the Inventors have now discovered a method of treatment of microalgae that advantageously enables to increase both their accumulation of TAG and also their productivity. More specifically, it has been shown that the accumulation of TAG in microalgae could be triggered by adding a source of the free radical, nitric oxide ($.N=O$, abbreviated NO), to the growth medium. As a further advantage, this method can be performed without need of reducing the supply of nitrate or of other nutrients, thereby allowing to also increase the productivity of TAG by microalgae. As an additional advantage, this method does not require blocking a metabolic pathway which can still be used for the proper functioning of the cell.

Within the framework of the invention, the term microalgae refers to eukaryote microalgae, notably to Diatoms.

Also in the sense of the present invention, the triacylglycerols also called triacylglycerides or TAG are esters resulting from the esterification of the three hydroxyl groups of glycerol, with three fatty acids. In the scheme below, TAG is synthesized by esterification of a glycerol backbone by three fatty acids ($R_1COOH$, $R_2COOH$, $R_3COOH$).

Scheme 1: Structure of TAG resulting from the esterification of the three hydroxyl groups of glycerol, with three fatty acids ($R_1COOH$, $R_2COOH$, $R_3COOH$).

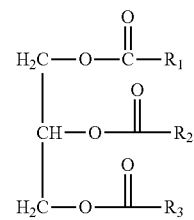

As used herein, the expression "trigerring the accumulation of TAG in microalgae" means that the cell content of TAG in said microalgae (weight of TAG per weight of microalgal cell) is increased as compared to that observed under normal nutritional and cultivation conditions, that is in non-stressful cultural conditions, notably in nitrogen sufficiency. The method according to the invention typically enables to increase the cell lipid production from [120] to [300]% compared to untreated condition.

As used herein, the term "productivity" or "biomass productivity" refers to the amount of TAG produced per volume of microalgal culture and per day and is expressed either by relative intensity of TAG, staining using Nile Red per liter and per day, or gram of TAG per liter and per day (g $l^{-1}$day$^{-1}$). The method according to the invention advantageously enables to reach a productivity comprised in the range of 0.025 to 1 g $l^{-1}$day$^{-1}$, in particular with Diatoms.

Thus, in one objet, the invention is directed to a method for triggering triacylglycerols (TAG) accumulation in microalgae comprising the step (i) of contacting a source of exogenous nitroxide (NO) with said microalgae in their growth medium.

In one aspect, the growth medium is nitrogen sufficient, that is a growth medium wherein the content of nitrates ($NO_3^-$) and/or nitrite ($NO_2^-$) is sufficient. It may notably contain from 0.5 mM to 10 mM of nitrates ($NO_3^-$) and/or nitrite ($NO_2^-$).

In another aspect, the microalgae are selected from microalgae of the Diatom phylum, the Chromalveolata phylum, and the Archaeplastidae phylum.

In a preferred aspect, the microalgae are selected from the Diatom micro-algae species *Phaeodactylum tricornutum* and *Thalassiosira pseudonana*, and the Archaeplastidae micro-algae species *Chlamydomonas, Ostreococcus, Chlorella*. More preferably, the microalgae are selected from the diatom micro-algae species *Phaeodactylum tricornutum* and *Thalassiosira pseudonana*. The source of exogenous nitroxide may be a nitroxide donor (NO donor), notably an organic nitroxide donor (organic NO donor).

As used herein, the terms "nitroxide donor" mean a molecular carrier of NO able to stabilize the NO radical until such time its release is required. Preferred NO donors include those able to release NO.

In a further aspect, the organic NO donor is selected from Diazeniumdiolates (NONOates), and S-Nitrosothiols.

Diazeniumdiolates [$R_1R_2N$—($N^+O^-$)=$NO^-$] consist of a diolate group bound to a nucleophile adduct, notably a primary or secondary amine or polyamine, via a nitrogen atom. NONOates decompose spontaneously in solution at physiological pH and temperature to generate up to 2 molar equivalents of NO, although prior cleavage of the molecule to release the terminal oxygen may be required (for example for V-PYRRO/NO and JS-K in the scheme below). Examples of NONOates can be found in publications (Miller et al., British Journal of Pharmacology (2007) 151, 305-321) and are represented in the following scheme:

Scheme 2: Examples of Diazeniumdiolates

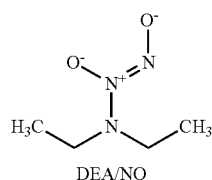

DEA/NO

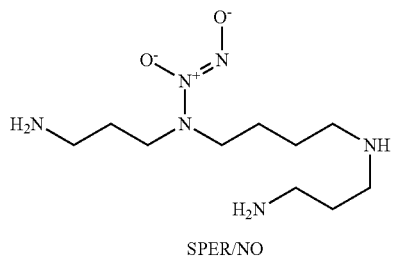

SPER/NO

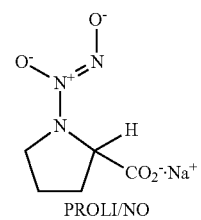

PROLI/NO

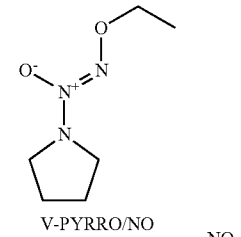

V-PYRRO/NO

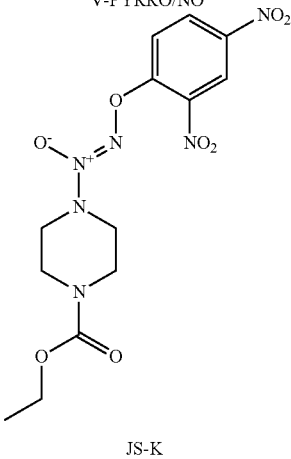

JS-K

S-Nitrosothiols class of NO donors covers a vast array of different compounds which contain a single chemical bond between a thiol (sulphydryl) group (R—SH) and the NO moiety. Examples of S-Nitrosothiols are reported in publications (e.g. Miller et al., British Journal of Pharmacology (2007) 151, 305-321) and include those reported in the following scheme:

Scheme 3: Examples of S-Nitrosothiols

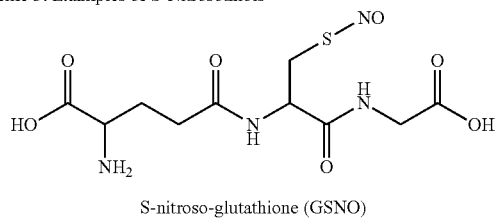

S-nitroso-glutathione (GSNO)

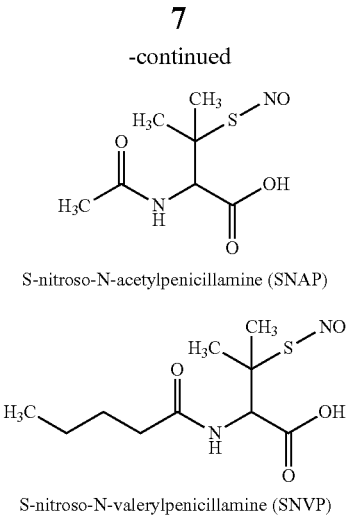

S-nitroso-N-acetylpenicillamine (SNAP)

S-nitroso-N-valerylpenicillamine (SNVP)

Preferably, the organic NO donor is a S-Nitrosothiol, notably selected from S-nitroso-N-acetylpenicillamine (SNAP), le S-nitroso-N-valerylpenicillamine (SNVP), S-nitroso-glutathione (GSNO).

The source of nitroxide may notably be incubated with the microalgae during 1 to 48 hours.

In a further aspect, the concentration of NO present or released in the growth medium is from 0.25 mM to 5 mM.

In another aspect, the method of the invention further comprises a step (ii) of recovering the accumulated triacylglycerols in microalgae, which may include one or more extraction steps. The extraction step may be implemented using solvents or another extraction method well known form the person skilled in the art.

According to a second object, the invention relates to the use of a method for triggering accumulation of triacylglycerols in microalgae as defined hereabove, for producing fatty acids, biofuels, pharmaceutical or cosmetic compositions or food supplements.

According to a further object, the invention relates to a method for producing biofuels comprising:
  steps (i) and (ii) as defined in the method for triggering accumulation of TAG hereabove;
  a step (iii) of transesterifying the triacylglycerols recovered in step (ii), for example as described in as described by Zhang et al., Bioresource Technology 147 (2013) 59-64; and optionally
  a step (iv) of recovering the obtained transesterified triacylglycerols.

According to an additional object, the invention relates to the use of exogenous nitroxide, notably of a NO donor, for triggering accumulation of triacylglycerols (TAG) in microalgae.

BRIEF DESCRIPTION OF THE DRAWINGS

In addition to the above provisions, the invention also comprises other provisions which will emerge from the remainder of the description which follows, and also to the appended drawings in which:

FIG. 1: Effect of increasing concentrations of SNAP on growth. Growth is measured in cell/mL.

FIG. 2: Effect of increasing concentrations of SNAP on TAG level per cell. TAG level per cell is given in relative fluorescence units/$10^6$ cells.

FIG. 3: Effect of increasing concentrations of SNAP on TAG productivity. TAG productivity is given in relative fluorescence unit (Rfu) corresponding to the fluorescence of Nile Red per mL and per day.

FIG. 4: NO release following treatment with 1 mM or 3 mM SNAP compared to the untreated control.

DETAILED DESCRIPTION

Examples

1) Materials & Methods

Figure 1:
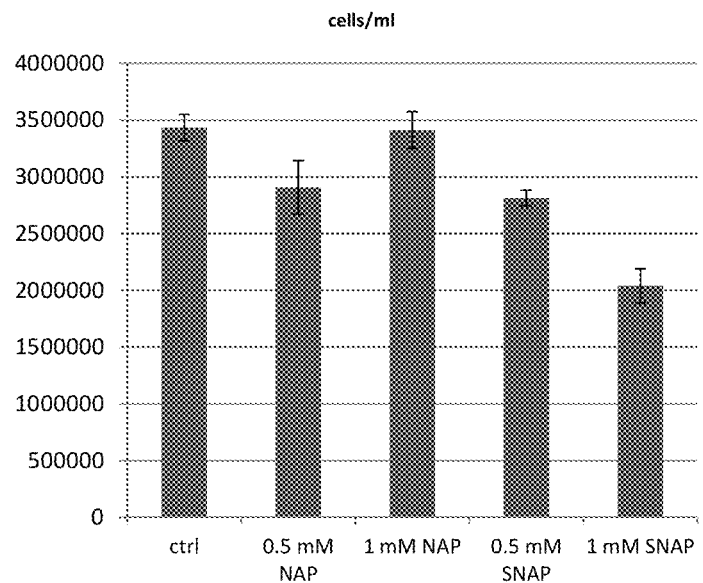
FIGS. 1 to 4: Effect of increasing concentrations of SNAP on the production of TAG in *Phaedocatylum tricornutum*. The medium used was 10×ESAW; incubation was performed in 500 μl, inoculated at 1E+06 cells/ml, with immediate addition of chemicals. Measurements were performed after 2 days of incubation. Data of FIGS. 1 and 2 and 3 are the results of 3 biological replicates, FIG. 4 was a time course without replicates. NAP was used as a non-active analogue of SNAP.

Cell Cultivation.

*Phaeodactylum tricornutum* (Ptl) Bohlin Strain 8.6 CCMP2561 (Culture Collection of Marine Phytoplankton, now known as NCMA: National Center for Marine Algae and Microbiota) was used in all experiments. Ptl was grown at 20° C. in 250 mL flask in artificial seawater (ESAW) medium (composition of the medium see table 1) using ten times enriched nitrogen and phosphate sources ($5.49 \cdot 10^{-3}$ M $NaNO_3$ and $2.24 \cdot 10^{-4}$ $NaH_3PO_4$) called "10×ESAW", or nitrogen-depleted medium. Cells were grown on a 12:12 light (30 μE $m^{-2}sec^{-1}$)/dark cycle. Cells were sub-cultured twice a week by inoculating $1 \cdot 10^6$ cells/ml with fresh media. Growth was evaluated by cell counting using a Malassez counting chamber, or by the absorption at 750 nm using a plate reader.

TABLE 3

Ingredients of solutions for ESAW 1 x cultivation medium..
ESAW-Medium Composition

| Reagents | Per Liter |
| --- | --- |
| NaCl | 21.19 g |
| $Na_2SO_4$ | 3.55 g |
| KCl | 0.599 g |
| $Na_2HCO_3$ | 0.174 g |
| KBr | 0.0863 g |
| $H_3BO_3$ | 0.023 g |
| NaF | 0.0028 g |
| $MgCl_2 * 6H_2O$ | 9.592 g |
| $CaCl_2 * 2H_2O$ | 1.344 g |
| $SrCl_2$ | 0.0218 mg |
| $NaNO_3$ | 46.7 mg |
| $NaH_2PO_4 * H_2O$ | 3.09 mg |
| $Na_2SiO_3 * 9H_2O$ | 30 mg |
| Metal Stock I | 1 ml |
| Metal Stock II | 1 ml |
| Vitamin Solution | 1 ml |
| Metal Stock I | |
| $Na_2EDTA * 2H_2O$ | 3.09 g |
| $FeCl_3 * 6H_2O$ | 1.77 g |
| Metal Stock II | |
| $Na_2EDTA * 2H_2O$ | 2.44 g |
| $ZnSO_4 * 7H_2O$ | 0.073 g |
| $CaSO_4 * 7H_2O$ | 0.016 g |
| $MnSO_4 * 4H_2O$ | 0.54 g |
| $Na_2MoO_4 * 2H_2O$ | 1.48 mg |
| $Na_2SeO_3$ | 0.173 mg |
| $NiCl2 * 6H_2O$ | 1.49 mg |

TABLE 3-continued

Ingredients of solutions for ESAW 1 x cultivation medium..
ESAW-Medium Composition

| Reagents | Per Liter |
|---|---|
| Vitamin Solution | |
| Biotin (Vitamin H) | 1 mg |
| Thiamine HCl (Vitamin $B_j$) | 100 mg |
| Cyanocobalamin (Vitamin $B_{j2}$) | 2 mg |
| pH = 8.2 | |

Incubation with a Nitric Oxide (NO) Donor Agent.

S-Nitroso-N-acetylpenicillamine (SNAP) is a compound that spontaneously releases NO, when dissolved. Nitrosoacetylpenicillamine (NAP) is used as a non-active compound, which does not release NO and can therefore be used for control experiments.

Measure of Nitric Oxide Using a Fluorescent Reporter

The fluorophore 4-amino-5-methylamino-2′,7′-difluororescein diacetate (DAF-FM) allows the sensitive detection of low levels of nitric peroxide ($ONOO^-$), which is in equilibrium with NO and thus indicates NO levels (St Laurent C D, Moon T C, Befus A D. 2015. Measurement of nitric oxide in mast cells with the fluorescent indicator DAF-FM diacetate. Methods Mol Biol. 1220:339-45) and was previously used to detect NO levels in *P. tricornutum* cells (Vardi et al., 2008). 10 ml culture were diluted to $10^6$ cells/ml and cells were incubated with 20 µl 5 mM DAF-FM (1.5 h, room temperature, darkness, shaking). Cells were washed and resuspended in 10 ml 10×ESAW media and aliquoted to 500 µl cultures on a 48 well culture plate to which the SNAP was added. For the examination of DAF-FM-dependent detection of nitric peroxide, 150 µl of the culture were transferred into a 96 well plate and fluorescence was measured with a TECAN infinite M1000Pro plate reader (excitation wavelength at 488 nm, emission at 529 nm).

Measure of TAG Accumulation by Nile Red Staining

Accumulation of TAG droplets was monitored by Nile Red (Sigma Aldrich) fluorescent staining (Excitation wavelength at 485 nm; emission at 525 nm) following the principles previously described (Abida et al., 2015). In brief, cells were diluted and adjusted to a cell density that was linearly correlated with Nile Red fluorescence. Nile Red solution (40 µl of 2.5 µg/mL stock concentration, in 100% DMSO) was added to 160 µl cell suspension. Oil bodies stained with Nile Red were then visualized using a Zeiss AxioScope.A1 microscope (FITC filter; Excitation wavelength at 488 nm; emission at 519 nm). The productivity, corresponding to the accumulation of TAG per volume and per time unit was calculated based on the staining by Nile Red, and expressed in relative fluorescence unit (Rfu) of Nile Red per mL and per day of incubation. Alternatively, Nile red fluorescence values were normalized to the cell concentration.

2) Results

Figure 2:
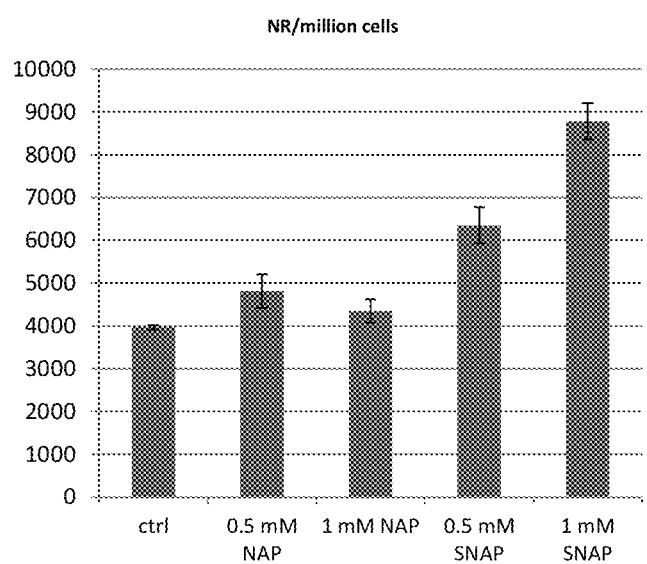
Figure 3:
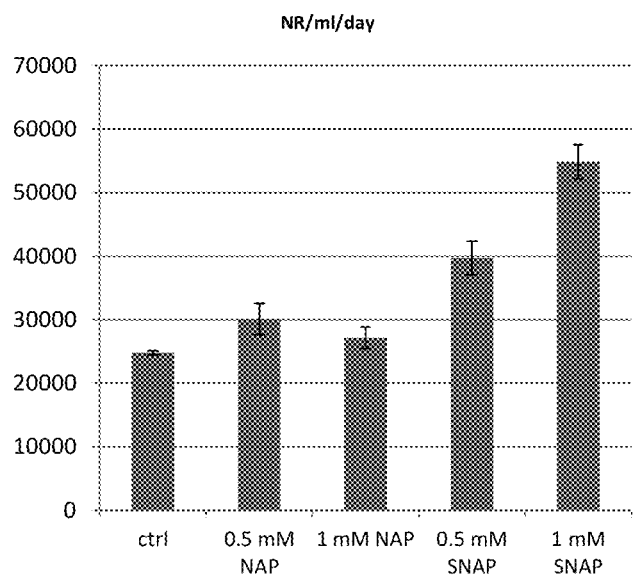
Figure 4:
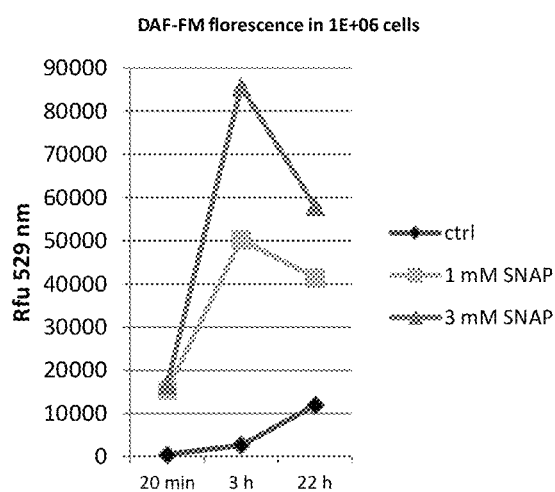

A 2-day incubation of *P. tricornutum* with 1 mM SNAP, in a 500 µL volume, induces a reduction of cell growth (FIG. 1), but triggers a 2.2 fold increase of TAG per cell (FIG. 2) and also a >2 fold increase of productivity, corresponding to the level of TAG per volume of culture and per day (FIG. 3).

The invention claimed is:

1. A method for triggering triacylglycerols accumulation in microalgae comprising the step (i) of contacting a source of exogenous nitric oxide with said microalgae in their growth medium, wherein the source of exogenous nitric oxide is an organic nitric oxide donor.

2. The method according to claim 1, wherein the growth medium contains nitrates ($NO_3^-$) and/or nitrites (NO2).

3. The method according to claim 1, wherein the microalgae is selected from the group consisting of microalgae of the Diatom phylum, the Chromalveolata phylum, and the Archaeplastidae phylum.

4. The method according to claim 3, wherein the microalgae is selected from the group consisting of Diatom micro-algae species *Phaeodactylum tricornutum* and *Thalassiosira pseudonana*, and the Archaeplastidae micro-algae species *Chlamydomonas, Ostreococcus, Chlorella*.

5. The method according to claim 1, wherein the nitric oxide donor is Diazeniumdiolates (NONOates) or S-Nitrosothiols.

6. The method according to claim 5, wherein the nitiric oxide donor is a S-Nitrosothiol.

7. The method according to claim 6, wherein the S-Nitrosothiol is selected from the group consisting of S-nitroso-N-acetylpenicillamine (SNAP), S-nitroso-N-valerylpenicillamine (SNVP), and S-nitroso-glutathione (GSNO).

8. The method according to claim 1, wherein the concentration of exogenous nitric oxide in the growth medium is from 0.25 mM to 5 mM.

9. The method according to claim 1, further comprising a step (ii) of recovering the accumulated triacylglycerols in microalgae.

10. The method according to claim 1, for further producing fatty acids, biofuels, pharmaceutical or cosmetic compositions or food supplements.

11. A method for producing biofuels comprising:
   steps (i) and (ii) as defined in claim 9;
   a step (iii) of transesterifying the triacylglycerols recovered in step (ii); and
      optionally a step (iv) of recovering the obtained transesterified triacylglycerols.

* * * * *